US005702428A

United States Patent [19]
Tippey et al.

[11] Patent Number: 5,702,428
[45] Date of Patent: Dec. 30, 1997

[54] ELECTRICAL STIMULATION FOR TREATMENT OF INCONTINENCE AND OTHER NEURO-MUSCULAR DISORDERS

[75] Inventors: Keith Edward Tippey, Knaresborough, United Kingdom; Jens Axelgaard, Fallbrook, Calif.

[73] Assignee: Axelgaard Manufacturing Company, Ltd., Fallbrook, Calif.

[21] Appl. No.: 694,458

[22] Filed: Aug. 1, 1996

Related U.S. Application Data

[62] Division of Ser. No. 335,750, Nov. 8, 1994, Pat. No. 5,562,717.

[30] Foreign Application Priority Data

May 23, 1992 [GB] United Kingdom ............ 9211085

[51] Int. Cl.$^6$ ........................................ A61N 1/32
[52] U.S. Cl. ................ 607/41; 607/72; 607/74; 607/138; 607/148; 607/152
[58] Field of Search ............... 607/39–41, 73, 607/74, 115, 138, 143, 148, 152

[56] References Cited

U.S. PATENT DOCUMENTS

| | | | |
|---|---|---|---|
| 5,010,895 | 4/1991 | Maurer et al. | 607/138 |
| 5,443,470 | 8/1995 | Stern et al. | 607/138 |
| 5,562,717 | 10/1996 | Tipey et al. | 607/41 |

FOREIGN PATENT DOCUMENTS

| | | | |
|---|---|---|---|
| 0116688 | 8/1984 | European Pat. Off. | 607/41 |
| 2717956 | 11/1977 | Germany | 607/138 |
| 3827232 | 11/1989 | Germany | 607/138 |
| 0584844 | 12/1977 | U.S.S.R. | 607/138 |

*Primary Examiner*—Jeffrey R. Jastrzab
*Attorney, Agent, or Firm*—Walter A. Hackler

[57] ABSTRACT

Electrical stimulation for the treatment of neuro-muscular disorders, in particular incontinence. A portable electrical stimulation apparatus for treatment of incontinence, comprising one or more electrodes (302) for applying one or more electrical stimulation signals to a patient's body, a signal generator for generating the electrical stimulation signal(s), one or more conductive leads for connecting the signal generator to the electrode(s), to deliver the electrical stimulation signal to the electrode(s); and a power supply, characterized in that the apparatus includes an instruction storage or a programming device for imparting a set of instructions to the signal generator, the signal generator being responsive to the instruction storage or programming device so that the generated signal adopts signal waveform characteristics selected in accordance with said set of instructions.

3 Claims, 10 Drawing Sheets

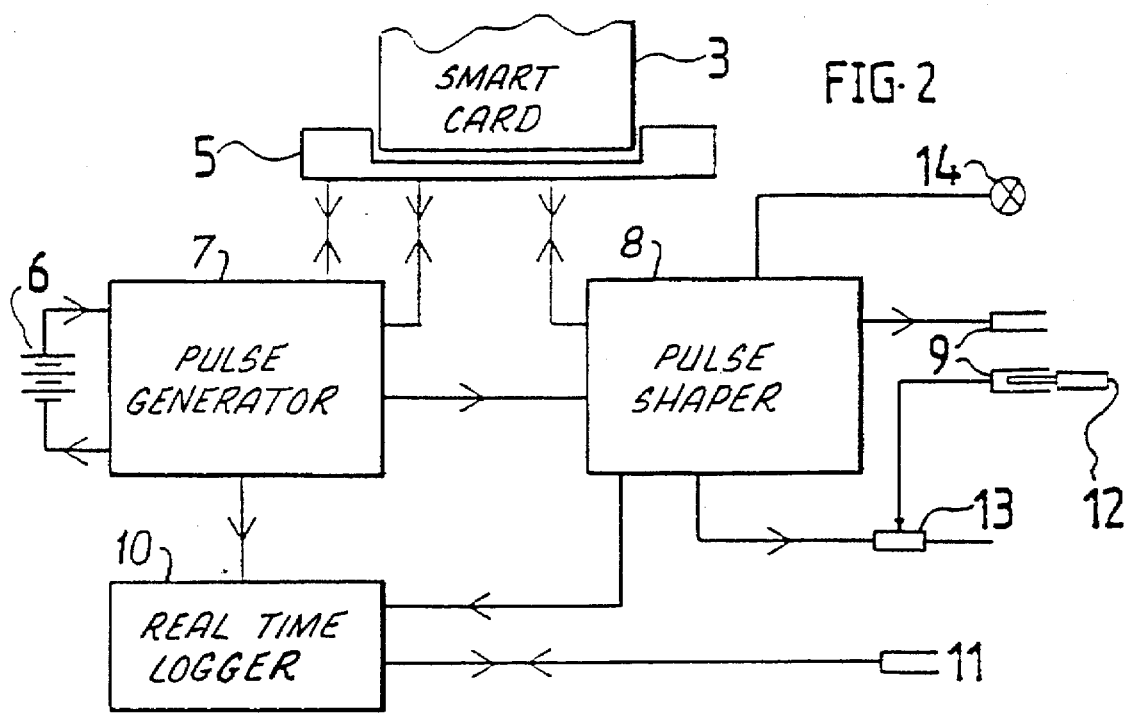
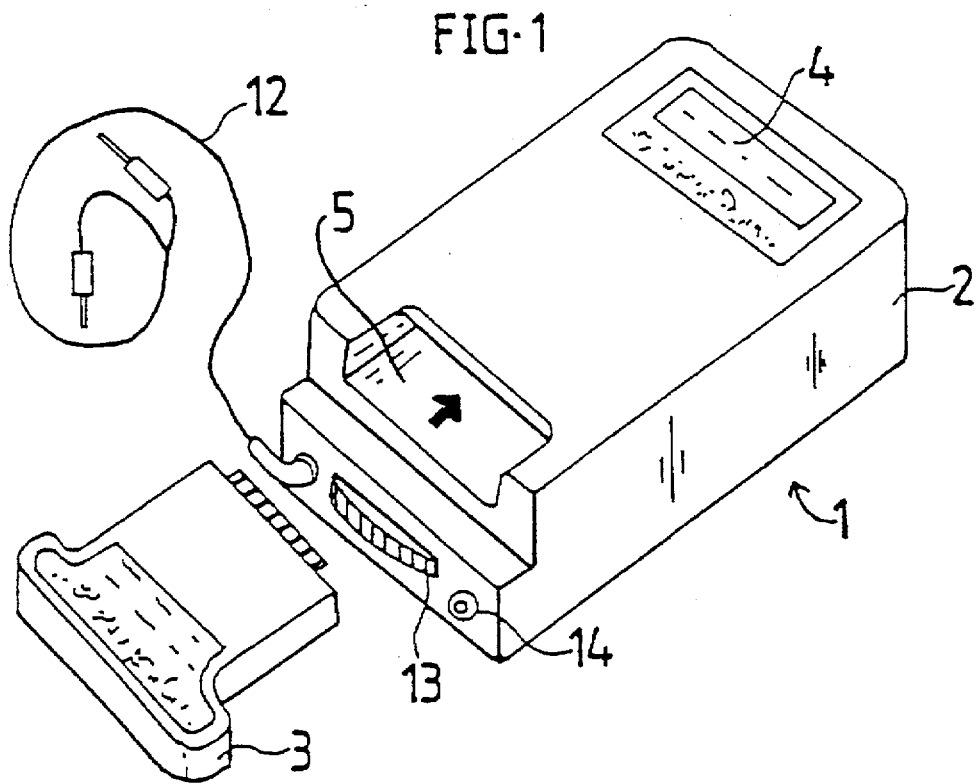

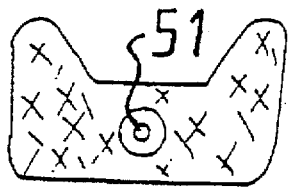
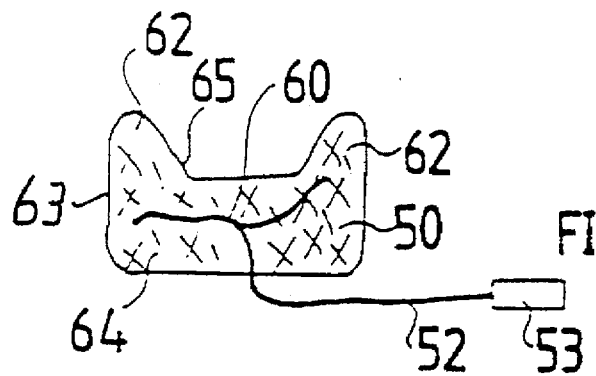
FIG. 3
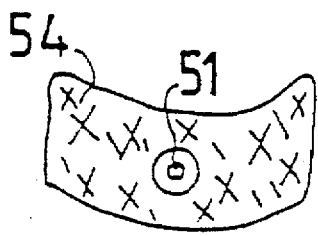
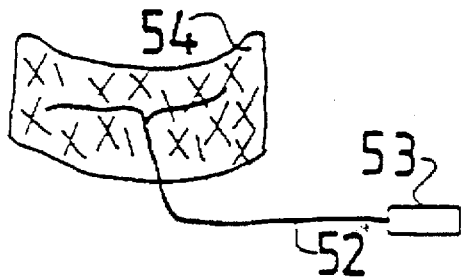
FIG. 4
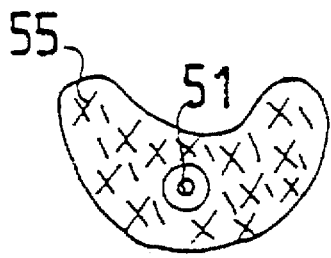
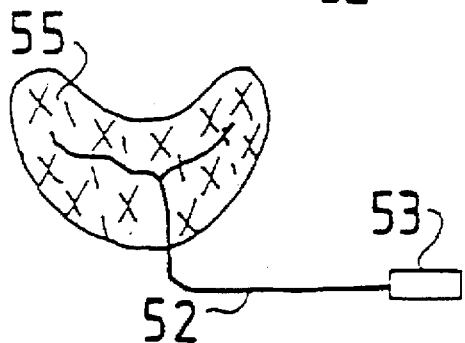
FIG. 5
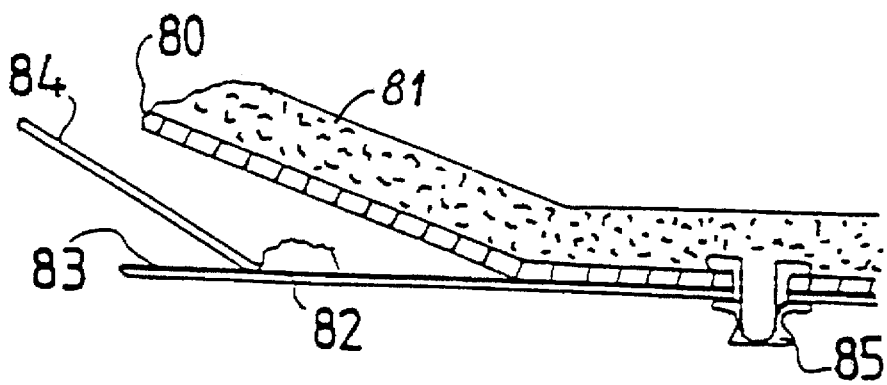
FIG. 8

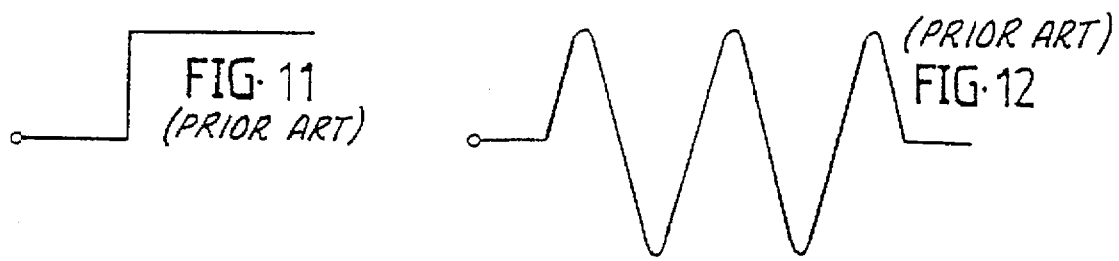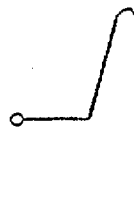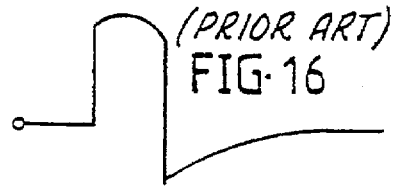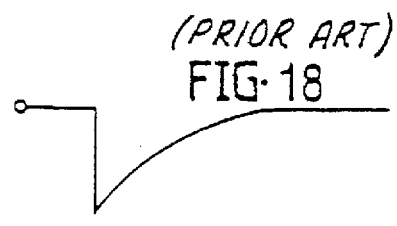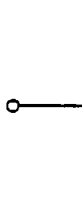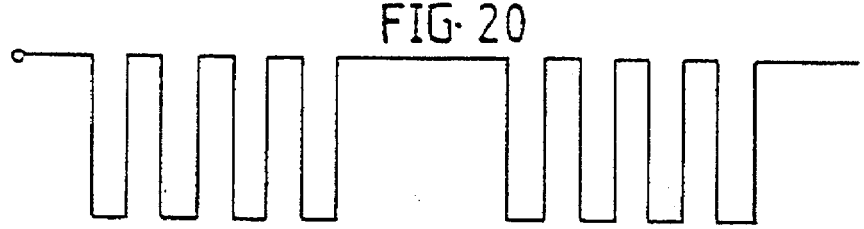

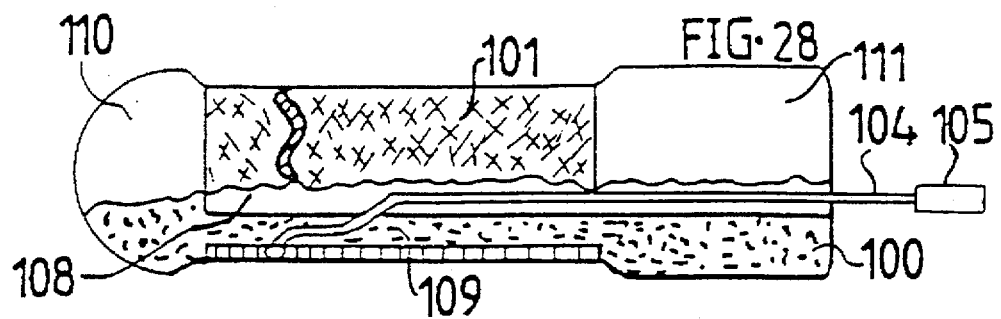
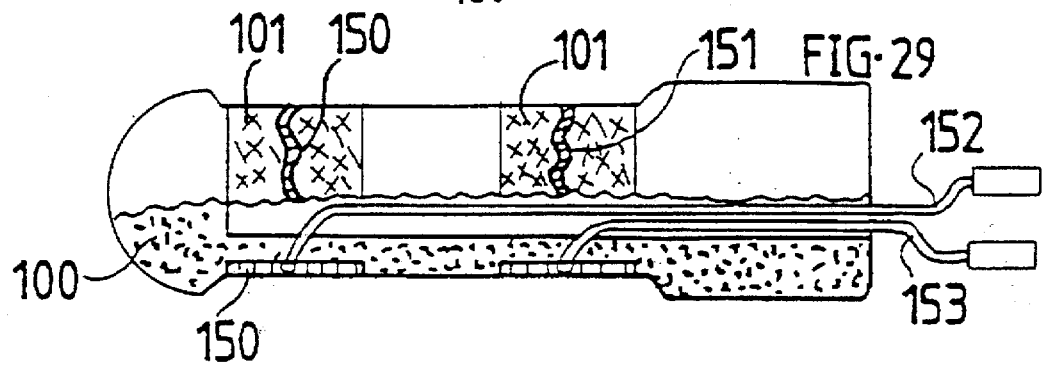
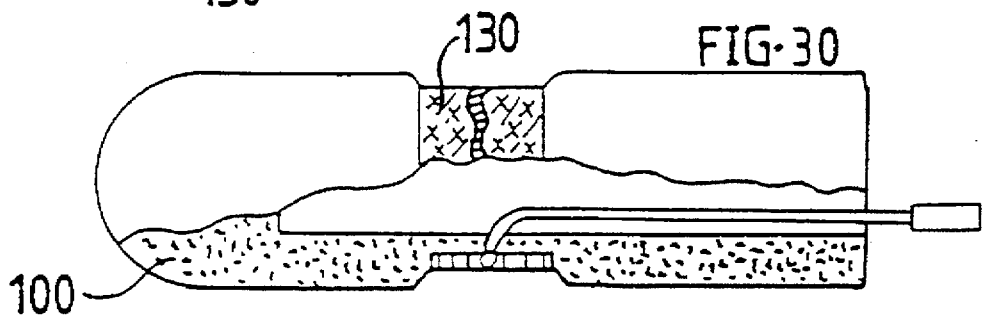
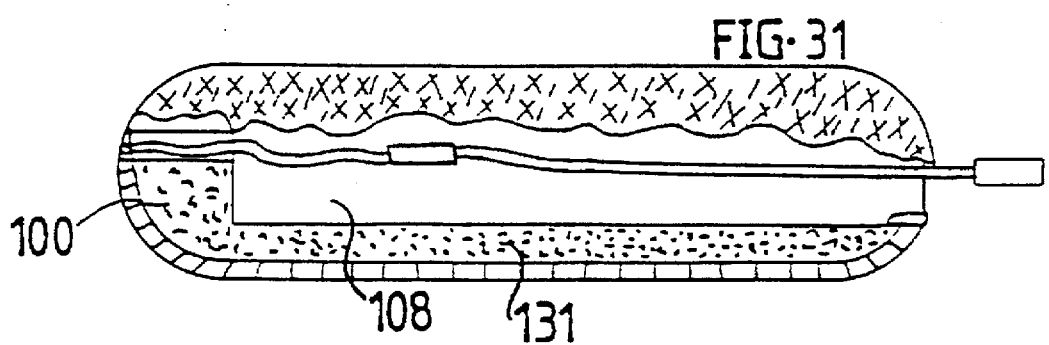
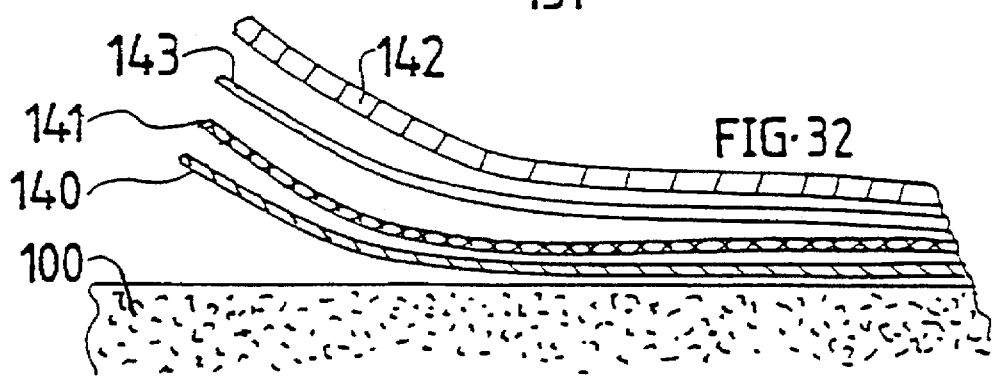

ELECTRICAL STIMULATION FOR TREATMENT OF INCONTINENCE AND OTHER NEURO-MUSCULAR DISORDERS

This application is a division of application Ser. No. 08/335,750, filed Nov. 8, 1994 now U.S. Pat. No. 5,562,7

TECHNICAL FIELD

The present invention relates to electrical nerve and muscle stimulation and particularly although not exclusively to electro-medical treatment for urinary and faecal incontinence, primarily in women but equally adaptable for men.

BACKGROUND ART

Conventional electro-stimulation treatments for urinary and faecal incontinence require a patient to apply stimulation via an internal electrode in electrical contact with the body. Treatment is applied for periods ranging from 10 minutes to several hours each day.

A conventional electro-stimulation system includes pulse generator housed in a portable battery box, and an electrode pad for attachment to the patient. Such systems are often used for the relief of chronic back pain or induced muscle contraction. These systems fall under the general classification of transcutaneous electrical nerve stimulation systems (TENS).

The above mentioned electro-stimulation systems conventionally use a drive signal to the electrode which is characterised by a sine wave, square wave, or spike impulse geometry, and is either monophasic, capacitively coupled monophasic, biphasic or asymmetric. Differing therapeutic effects are achieved using different drive signal types. Conventionally such stimulation systems allow for a variation of drive signal pulse width or frequency by the patient. However each such known portable stimulation system has electronics which are dedicated for providing a specific predetermined drive signal having a geometry and other characteristics matched to the intended therapeutic effect. Adjustment of the control signal is conventionally provided by electronic push switches and or rotational control knobs. Such switches and knobs can often be tampered with by the patient, and it is thus difficult for a medical practitioner prescribing electro-stimulation treatment to control the treatment when the patient is away from a clinic.

Other known electro-stimulators include microprocessor based units, but these have a problem that conventionally, specialised pre-programming equipment needs to be used at the clinic to set the signal parameters. Such equipment is expensive and often difficult to use.

Specific embodiments of the present invention aim to provide electro-stimulation apparatus which can be adjusted and preset by a medical practitioner, medical assistant or clinician without requiring of them electronic or computer literacy, and once set is tamper proof by a patient.

In the treatment of incontinence, it is known to use a vaginal or rectal electrode comprising a moulded plastic plug which is insertable into the body. Such plugs may be rigid, semi-rigid or of the expanding coil type. However, these known internal electrodes are uncomfortable and problematic due to their fixed size, difficulty to insert and poor contact with the body, producing uncomfortable sudden increases in pulse strength. Subsequently, patients dislike such treatments and compliance with the treatment is poor.

Surface electrodes of metal, metallised foil, carbonized rubber and other similar thin conductive plate materials are known. However, such materials are insufficiently flexible and can be problematic causing discomfort, soreness and subsequently poor compliance to treatment. The known surface electrodes are unsuitably shaped and sized, and insufficiently flexible for application over the perineal region adjacent to the vaginal and rectal tracts.

Prior art cloth electrodes are known from U.S. Pat. No. 5,038,796 and U.S. Pat. No. 4,708,149. These electrodes are designed for functional electrical stimulation (FES) and the symptomatic treatment of such afflictions as arthritic pain and back pain.

Pelvic Floor Exercises are a known treatment for exercising muscles which control the urinary function. Such exercises require levator ani muscles to be contracted and relaxed regularly during the course of a day or over a period of many weeks, often months.

A known aid for such exercises comprises a pre-formed core of rigid plastics material. Such aids are provided in a set of graded weights, requiring the (female) patient to insert them into a vaginal tract, and retain them in position. However, this is difficult for many patients, because commonly the smallest available weight available is too heavy, or the size is incorrect. Insertion and renewal of the cores can be problematic.

Another type of known device comprises a foam cushion, which is used to apply pressure at the bladder neck, keeping the bladder neck closed during normal movement and exercise. However, such devices are not intended for, and are unsuitable for performing Pelvic Floor Exercises. The devices must be softened with water prior to use.

DISCLOSURE OF THE INVENTION

Specific embodiments of the present invention aim to address the problems associated with conventional plug type electrodes, and the problems encountered in the treatment of incontinence.

Specific embodiments of the present invention aim to provide an improved Pelvic Floor Exercise apparatus.

According to one aspect of the present invention there is provided a portable electrical stimulation apparatus for treatment of incontinence disorders, comprising:

one or more electrodes for applying one or more electrical stimulation signals to a patients body;

a signal generator for generating the electrical stimulation signal(s);

one or more conductive leads for connecting the signal generator to the electrode(s), to deliver the electrical stimulation signal to the electrode(s); and a power supply, characterised in that the apparatus includes an instruction storage means or a programming means for imparting a set of instructions to the signal generating means, the signal generating means being responsive to the instruction storage means or programming means that the generated signal adopts signal waveform characteristics selected in accordance with said set of instructions.

Preferably at least one electrode is applied in the vaginal or anal region, and at least one electrode is a surface electrode to be applied to a surface of the patients skin.

Preferably the waveform characteristics of the electrical stimulation signal are not alterable by the patient, the waveform being determined from normal neuronal activity of the patient and applied so as to superimpose the normal neuronal activity.

Preferably said instructions comprise instructions on the selection of one or more of the following signal waveform characteristics:

pulse geometry type;
pulse width magnitude;
pulse train frequency;
pulse envelope type;
pulse envelope duration;
pulse envelope duty cycle;
treatment time;
signal intensity.

Preferably the pulse envelope duration is in the range 1 to 100,000 microseconds.

Preferably the pulse train frequency is in the range 200 Hz to 5 MHz.

Preferably the envelope duty cycle is in the range 1 to 99%.

Preferably the number of pulses per each envelope is in the range 1 to 20,000.

Preferably the pulse envelope is of a sinusoidal, square wave or saw tooth wave type.

Preferably the frequency with which the envelope occurs is in the range 0.1 to 2,000 Hz.

The pulse envelope may occur at a time in the duty cycle, which is random between successively generated envelopes.

Preferably the instruction storage means is a smart card.

Preferably the programming means is a personal computer.

Preferably the apparatus has a data logging means for recording generation of the electrical stimulation signal, so as to provide a record of how often the electrical stimulation signal has been generated.

According to a second aspect of the present invention there is provided an electrode characterised by being adapted to attach to the surface of a perineal region, and an electrode characterised by being attached to the lower sacral region. Said electrodes comprise a flexible conductive substantially sheet material.

Preferably, said electrodes are adaptable for use in the treatment of incontinence. The flexible conductive sheet material preferably comprises a woven or knitted cloth.

Said woven or knitted cloth may contain conductive fibres of stainless steel, gold or other electro plated precious metals.

Preferably said electrode further comprises a waterroof backing.

Preferably said electrode is attachable to a perineal region using a conductive adhesive gel.

Said electrode may have a stud fixing.

Preferably, said electrode has a pigtail type electrical connector.

Preferably a length of said electrode is in the range 20 to 100 millimetres, and is suitably in the range 40 to 60 millimetres.

Preferably a width of said electrode is in the range 10 to 60 millimetres, and is suitably in the range 20 to 40 millimetres.

The shape of the electrode may be such that it has one or more concave perimeter portions. The electrode may have one or more convex perimeter portions.

Preferably, the electrode has an electrical plug connection, and may have an electrical connection lead.

The electrode may have an elongated centre portion of a first width and one or more protruding end portions of a second width, wherein said second width is greater than said first width.

According to a third aspect of the present invention, there is provided an electrode which is adapted to be insertable into an anatomical cavity or tract, said electrode comprising a plug of a substantially expandable and/or compressible material.

The flexible and compressible construction of the internal electrode is such that it can be compacted into tampon form for ease of insertion, hygiene and comfort. Once in place, the tampon will expand and provide electrical contact with the vaginal/anal walls.

Said material may be a foam material.

Said material may be a polyvinyl formal foam (PVF) material.

Said material may be a paper or cotton material.

Said electrode may further cornprise a conductive sheath surrounding at least partially said plug.

Said conductive sheath may be of a woven or knitted cloth.

Said electrode may further comprise a conductive lead adapted for carrying a drive signal to said conductive material and for removing said plug from said cavity.

Said electrode may be adapted (or insertion of a rigid support member to support the electrode during insertion of said electrode into said cavity or tract, said support member being removable once said electrode is deployed therein within said cavity or tract.

Said electrode may be adapted for deployment in said cavity or tract by insertion of a hollow tubular applicator containing said electrode in compression, in to said cavity or tract, followed by subsequent removal of said applicator from the cavity or tract, allowing expansion of said electrode within said cavity or tract.

According to a fourth aspect of the present invention there is provided a tampon electrode for insertion into the vagina or anus of a patient, the electrode comprising:

an outer sheath having a conductive outer surface for imparting an electrical stimulation signal to the vaginal or anal wall; and a conductive lead for sttpply of the electrical stimulation signal to the electrode;

characterised in that the ottter sheath is expandable and contractible such that the sheath can be inflated or deflated whilst in position in the vagina or anus.

Preferably the electrode has a rigid inner member around which the outer sheath is arranged, such that when the electrode is in the deflated condition, the rigid inner member lends the electrode sufficient rigidity so as to enable the electrode to be pushed into the vagina or anus for insertion therein.

Preferably the electrode has a fluid supply tube connected thereto for delivery of a pressurised fluid to the electrode for inflation thereof.

Preferably the electrode is inflatable by an increase in air pressure within the outer sheath.

Preferably the outer sheath is of an elastic material.

Preferably said elastic material is a silicon rubber.

Preferably the conductive outer surface comprises a woven or knitted conductive cloth attached to the outer sheath.

According to a fifth aspect of the present invention there is provided a sensing apparatus for sensing the condition of muscles in the vagina/or anus region, characterised by comprising:

a tampon electrode for insertion into the vagina or anus, the tampon electrode capable of transmitting a pressure signal in response to an increase in pressure exerted on the electrode bv the vaginal or anal muscles;

a pressure sensor means for sensing the signals the pressure sensing means producing an output dependent on the pressure exerted on the electrode by the vaginal or anal muscles.

Preferably the pressure signal is a pneumatic signal or an hydraulic signal, generated in response to pressure exerted on an expandable or contractible electrode.

Preferably the electrode is inflatable and there are provided means for inflating the electrode.

The electrode may have a conductive outer surface for applying an electrical stimulation signal to the vaginal or anal region, and the sensing apparatus includes a signal generator for generating the electro-stimulation signal, and may include a condtuctive lead for delivery of the electrical stimulation signal from the signal generator to the electrode.

Preferably the apparatus has an electro-myographic or perineometer sensor, which receives an electrical signal from the conductive outer surface of the electrode via the conductive lead, the signal generator being arranged to produce an electro-stimulation signal in response to an output from the electro-myographic or perineometer sensor.

The apparatus may be adapted for use as a means of facilitation of muscles in the vaginal region or anal region.

Preferably the apparatus has a display and a data recording means.

The present invention may provide a multiplexed combination of transcutaneous surface electrodes and/or internal vaginal/anal electrodes. The electrical characteristics of the said electrodes are provided by woven or knitted conductive fabric which ensures uniform current distribution and maximum comfort and hygiene.

The invention may provide a pulse generator which is convenient and simple for the patient to operate. Preferably, the pulse generator incorporates a data logging system to record patient compliance to treatment. Multiplexed pulse parameters can be preselected by the clinic for specific treatments by insertion of the specially preprogrammed Smart Cards such as those using the PCMCIA Interface Standard.

Treatment parameters may be down loaded from a PC into an integral memory using specially prepared software which initiates the specific parameters according to a patient's case history and symptoms. Preselected parameters loaded into the pulse generator are not available to or adjustable by the patient and which ensures strict compliance to the specific treatment regime.

Pulsed currents are delivered by the pulse generator, via the transcutaneous conductive surface electrodes which have specific anatomical placement to stimulate the dorsal and perineal branches of the pudendal nerve as they arise above the lower facia of the uro-genital diaphragm.

Pulsed currents may also be applied directly to the fibres of the levator ani muscle through the vaginal or anal walls using the tampon electrode. Pulsed currents may also be applied via a combination of the tampon and the surface electrodes to direct the current to specific muscles/nerve groups.

The present invention may provide for such pulsed currents to be supplied in variable frequency envelopes which are concomitant with normal neuronal activity determined from similar, but healthy nerve/muscle groups. The effect of such specific treatment currents is to re-establish neuronal motor and sensory control and to increase the population and fatigue resistance of the type I postural muscle fibres which are responsible for uretheral and anal closure.

Provision is also made within the preset parameters to strengthen the type II muscle fibres responsible for additional effort, support and reflex closure during physical stress conditions.

The present invention may also provide for an inflatable tampon electrode which can be used A) to apply the preset treatment parameters through the vaginal and/or anal walls, or B) as an electromyographic perineometer sensor to measure improvement achieved by the treatment and to provide encouragement for the patient to continue, or, C) as a means of Facilitation to provide a combined voluntary and F.E.S induced muscle exercise programme.

Any of the said tampon electrodes can be used solely or in combination with the cutaneous electrodes.

The invention includes a portable electrical stimulation apparatus comprising;

a signal generating means for generating an electrical signal; and a preset instruction means, or a preset programming means, for imparting instructions to the signal generating means.

wherein the signal generating means is responsive to the programming means such that the generated signal can adopt characteristics selected in accordance with said instructions.

Preferably, said programming means comprises a memory storage device pre-programmed with said instructions.

Preferably, the memory storage device is detachable from said signal generating means.

Preferably, the apparatus has a plurality of said memory storage devices, each substitutable for one another.

Each individual said memory storage device may be pro-programmed with a different set of instructions to each other memory storage device. Preferably, the apparatus further comprises a signal processing means for producing an electrical drive signal in accordance with any of said instructions. Said memory storage device may be permanent within the apparatus and can be programmed via a personal computer using software routines which generate the said parameters from data input in respect to patient history and symptoms. The said software may comprise user friendly windows with relevant prompts for every aspect of treatment to be considered. A user option is provided to allow final parameter adjustment within predetermined limits. Thus a set of said memory storage devices may be provided, each containing instructions to the signal generating means for generating a signal suitable for treatment of a particular disorder.

The apparatus may have a patient-adjustable means of varying the intensity of an electrical drive signal to an electrode.

According to a further aspect of the present invention, there is provided a portable electrical stimulation apparatus comprising a drive signal generation means and recording means for recording data regarding operation of the drive signal.

Said recorded data may include the frequency and/or duration of a time period in which said drive signal is actively conducted through living tissue. This may provide a strict compliance record of stimulation applied to the body. Said recording will not register if electrodes become detached or short circuited.

Said recording means may be interrogatable to display parts of said data. Said recording means may be interrogatable by a personal computer via a data port, said data port comprising part of the apparatus.

Said recording means may also be embodied within a Smart Card or Flash Card with random access memory (RAM) or non volatile memory. Said storage device will preferably be portable and be able to transmit and receive stored data berween a personal comuputer and the signal generator.

According to another aspect of the present invention, there is provided an electrode which can be attached to another part of the external anatomy such as a buttock. This indifferent electrode would preferably be used with monophasic or a symmetrically balanced pulse geometry where stimulation at the indifferent is unimportant to the treatment.

As such, this electrode may be of arbitrary shape and size, but will preferably be of twice the conductive surface area to that of the perineal electrode to provide a wider dispersal of the current at the indifferent electrode position over the sacral plexus.

Said indifferent electrode is preferably of specific shape and size to mould comfortably over the sacral spine, spinous processes, S2, S3 and S4. Said position is preferable to provide stimulation using balanced byphasic pulse geometry over the sacral nerve routes from where the urinary and faecal control nerves originate.

The invention provides for an electrode adapted to be insertable into an anatomical cavity or tract, said electrode comprising a core of a substantially expandable and/or compressible material.

Said material is preferably substantially deformable and resilient.

Preferably, the electrode further comprises a conductive sheath surrounding at least partially said core.

Preferably, said conductive sheath is of a woven or knitted fibre, for example stainless steel, gold or other electro-plated precious metal.

Preferably, the tampon electrode further comprises a conductive lead adapted for carrying a drive signal to said conductive material and for removing said electrode from said cavity.

The core may have a hollow passage for the insertion of a rigid member for supporting the core during insertion into the cavity or tract.

Said tampon electrode may have a first said conductive sheath and a second said conductive sheath, said sheaths being electrically isolated from each other, said sheaths having respective first and second electrical connection means thereto.

Said first and second sheaths may be driven by respective first and second driving signals.

Said first and second driving signals may be substantially identical or may be substantially dissimilar to each other.

The invention includes use of a said tampon electrode having first and second conductive sheaths in F.E.S. treatment of incontinence.

The invention provides for a plug having a core of a resilient deformable material for insertion into a human vaginal or rectal tract.

Preferably, said core material ohardnd electrode or plug has a Shore hardness of below 45.

Suitably, said material has a Shore hardness of less than 30.

Said material may be a foam material, for example a polyvinyl formal foam (PVF) material. Said material may be a paper or cotton material.

An electrode or plug according to the fourth or fifth aspects may be adapted for insertion of a rigid support member to support the electrode during insertion of said electrode into said cavity or tract, said support member being removable once said electrode is deployed therein within said cavity or tract.

A said electrode or plug according to the fourth or fifth aspect may be adapted for deployment in said cavity or tract by insertion of a hollow tubular applicator containing said electrode in compression into said cavity or tract, followed by subsequent removal of said applicator from the cavity or tract, allowing expansion of said electrode within said cavity or tract.

Preferably an electrode and/or plug according to the fourth or fifth aspect has a length in the range 30 to 100 millimetres.

Suitably, said length is in the range 45 to 65 millimetres.

Preferably, the electrode and/or plug has a width or diameter in the range 10 to 40 millimetres.

Suitably, the width is in the range 20 to 30 millimetres.

The invention provides for an inflatable tampon electrode. Said inflatable tampon electrode may have a gossamer, non-conductive outer sheath. Said outer sheath may be a silicon rubber. Said outer sheath may incorporate an integral conductive band. Said conductive band may be a substantially sheet material.

Said sheet material may be of woven or knitted conductive cloth. Said conductive cloth may be woven or knitted fibre, for example stainless steel, gold or other electro-plated precious metals. Said conductive cloth may extend internally to form the connecting means to a pulse generating apparatus. Said connecting means may also provide a means of obtaining electromyographic (EMG) readings and recordings.

Said connecting means will pass through a semi-rigid tube which may be used to insert the tampon prior to treatment. Said semi-rigid tube will provide a means to pass air into the outer flexible sheath such that the outer sheath may be inflated until it is in contact with the internal walls of the patients body cavity. Said air tube and electrical connection is preferably connected to a monitoring and stimulating apparatus, preferably incorporated into the pulse generator.

Said apparatus may comprise an air pump to inflate the tampon, and a pressure sensor to monitor internal air pressure and to cut off the air supply to the tampon when a predetermined level of air pressure is reached. Said sensor may determine a volumetric inflation required to attain a resting tone pressure of the muscles surrounding the inflatable sheath and may detect any increase caused by contraction of the surrounding muscle. Such a measurement may indicate a patient's progress and improvement due to the main stimulation treatment.

Said sensor may be used to facilitate stimulating pulses in response to pressure increase due to voluntary muscle contraction. Said stimulating pulse will cause further muscle contraction and further aid strengthening. Through this facilitation, the patients voluntary muscle strength will be enhanced by muscle stimulation. Said pulse parameters may be any of those previously described. Said apparatus may store data in a memory for later analysis. Said apparatus may provide a visual display which a patient may use to work to a daily exercise/facilitation routine with specified targets and visual achievements.

The invention incit,des a compilation of an electrostimulator apparatus as above, a selection of stimulator electrodes as above, a selection of programming modules each programmed for a different type of treatment, a plurality of treatment instruction cards corresponding with the modules and giving instructions for the administration of treatment by the patient and/or clinician in accordance with the mo[,] and an instruction guide on the use of the apparatus, which may also be incorporated in the Smart Card.

The invention includes a method of treatment of incontinence using electrical stimulation of a perineal region by a flexible substantially sheet material electrode.

The invention includes a method of treatment of incontinence using Pelvic Floor Exercises and Bio eedback using an electrode or plug as described in the fourth or fifth aspects.

The invention includes a method of monitoring a patients' progress, and determining an improvement in pelvic floor tone and strength.

DESCRIPTION OF THE DRAWINGS

For a better understanding of the invention, and to show how the same may be carried into effect, reference will now be made, by way of example, to various specific embodiments of the invention as shown in the accompanying diagrammatic drawings in which:

FIG. 1 shows a portable [r]ve module according to a specific embodiment of the present invention or driving an electrode;

FIG. 2 shows a schematic circuit diagram of the drive module;

FIG. 3 shows in plan view a first cutaneous electrode pad according to a another specific embodiment of the present invention;

FIG. 4 shows in plan view a second cutaneous electrode pad according to a further specific embodiment of the present invention;

FIG. 5 shows in plan view a third cutaneous electrode pad in accordance with vet another embodiment of the present invention;

FIG. 8 shows a construction of the embodiments of FIGS. 3 to 7;

FIGS. 11 to 19 show various prior art pulse geometry components;

FIG. 20 shows part of one example of an electrical stimulation drive signal according to the present invention;

FIGS. 24 shows as an example according to the present invention, a part of an electrical stimulation drive signal having uniform fixed rate envelopes;

FIG. 25 shows as an example according to the present invention, a form of electrical stimulation drive signal having a randomly generated envelope;

FIG. 26 shows as an example according to the present invention, a form of electrical stimulation drive signal having sequentially generated envelopes;

FIG. 28 shows a second insetrobie electrode according to another embodiment of the present invention;

FIG. 29 shows a third insertable electrode according to another embodiment of the present invention;

FIG. 30 shows a fourth insertable electrode according to another embodiment of the present invention;

FIG. 31 shows a fifth insertable electrode according to another embodiment of the present invention;

FIG. 32 shows a construction of part of an insenable electrode according to an embodiment of the present invention;

BEST MODE FOR CARRYING OUT THE INVENTION

Figure 6:
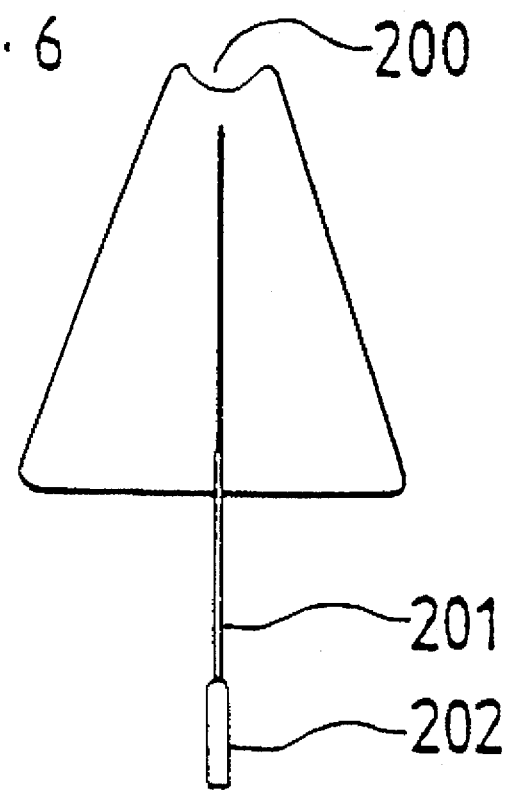
FIG. 6 shows in plan view an electrode for positioning on the sacrum of a patient, according to another embodiment of the present invention.

An electro-stimulation apparatus according to a specific embodiment of the present invention comprises a drive module and a stimulation electrode arranged to be driven by the drive module.

Referring to FIGS. 1 and 2 of the accompanying drawings, a drive unit 1 comprises a portable case 2 which contains an electric battery power supply, 4, and electronics (not shown in FIG. 1). The drive unit has a detachable instruction storage or programming means such as a smart card 3 and further comprises a clip for attaching the drive unit to an item of clothing, for example a belt.

The smart card 3 is attachable to the electronics of the drive unit 1 via a connection socket 5 and is detachable such that it can be replaced by a substitute Smart card.

The drive unit further features an intensity control 13 for controlling the intensity of the drive signal to the stimulator electrode, the intensity control being of a type which can be altered by the patient, and an indicator lamp 14 to indicate when the drive signal is operating and/or whether the battery is charged. A liquid crystal display (LCD) may also be provided to show the status of the device.

Referring to FIG. 2 of the accompanying drawings, a schematic diagram of the electronics of the drive unit of FIG. 1 is shown. The electronics comprises the socket 5 for accepting the Smart Card 3, a battery power supply 6 for supplying power to the electronics, a pulse generator 7, an output pulse shaper 8 for modifying the output of the pulse generator 7 and outputting a drive signal, a plurality of output sockets 9 connected to the output pulse shaper 8 and providing an output path for the drive signal, an intensity control 13, which is, for example a thumb wheel variable resistor, a real time logger 10 for recording parameters of the output of the pulse generator and/or drive signal and an external connector 11, for example a serial port through which the real time logger 10 can be interrogated periodically using separate interrogation equipment, for example a personal computer, and the battery charge/signal output indicator 14.

The output socket 9 is connectable to a stimulator electrode, which is driven by the drive signal via an output electrode lead 12 from the drive unit.

The electrode lead 12 is preferably of a high flex material such as silicon rubber, having standard 2 mm plug pins or press-stud type fasteners for connecting to the stimulator electrode.

The Smart Card may be either pre-programmed or programmable using a standard PC. The smart card module could be replaced by some other instruction storage or programming means, e.g. an audio cassette, or an internal ROM programmable externally of the drive unit. Hereafter, for convenience, the instruction storage or programming means will be referred to as a Smart card.

In use, the drive module operates as follows. The pulse generator, produces a pulse signal in response to programmed instructions stored in the smart card 3. The pulse signal is then modified by the output pulse shaper 8 in accordance with the instructions stored in the Smart card. A drive signal appears at the output of the pulse shaper, on the output lead 12, and is supplied to the output socket 9 connected to the stimulation electrode.

Each smart card may be supplied either pre-programmed or programmable using a standard personal computer. Each pre-programmed smart card is clearly marked with the parameters of the drive signal which the card is programmed for producing, together with the type of therapeutic treatment to which these parameters relate. For example, a smart card may be marked with the following information, and programmed accordingly with instructions for generating electrical stimulation drive signal having corresponding waveform characteristics.

Treatment, URINARY STRESS INCONTINENCE
Pulse geometry-square biphasic
Pulse width—200 μsecs
Pulse envelope frequency—Random 5–40 Hz
Pulse envelope—100 msecs
Exert/relax—8 see cycle 50% duty cycle
Treatment time—2 hours
Intensity—0–30 Ma.

In other Smart cards for other treatments, variations upon the above drive signal characteristics may be made. For example any of a number of drive signal characteristics may be varied.

The real time logger 10 records details of the pulse signal output from the pulse generator 7 through normal biological body impedance. Stimulation pulses generated during electrode disconnection or short circuit will not register on the data logger or Smart Card. Compliance of the output drive signal can be monitored and checked against treatment prescribed by a clinician. The recorded data shows whether a treatment has been administered on a regular basis, without any parameters of the drive signal being tampered with by the patient.

In use in a clinical situation, a complete electro-stimulator apparatus comprises a selection of stimulators, a selection of modules each programmed for a different type of treatment, treatment instruction cards corresponding with the modules and giving instructions for the administration of treatment by the patient and/or clinician, a battery recharger, (where required) and a full instruction guide on the use of the apparatus.

FIGS. 3 to 7 of the accompanying drawings show various embodiments of transcutaneous electrode pads suitable for perineal application. Such electrodes are suitable to be driven by the drive unit described with reference to FIGS. 1 and 2.

The electrode pads are constructed from woven or knitted electrically conductive cloth, mounted on a thin flexible and waterproof material and coated in a self-adhesive conductive gel. The conductive gel is of a known prior art type, and in one version is formulated to be adjustable in adhesive strength by the addition of water.

The first embodiment electrode 50 shown in FIG. 3, a stud fastener 51 and a pigtail cable 52 having a socket 53 for connection to for example the output socket 9. Where a pigtail connection is used the conductive elements of the cable 52 may be extensions of the woven material of the electrode 50. Connection of the conductive elements to the plug 53 may be by moulding the elements into the plug, by sewing the elements into the plug after moulding, by adhesive bonding using a conductive adhesive or by ultrasonic welding. Similarly, the conductive elements of the cable 52 may be adhesively bonded to, or ultrasonically welded to, or sewn into the woven material of the electrode 50.

The electrode is shaped as shown, having an elongate strip 60 of a first width having projections 62 of a second width at each end. A perimeter 63 has one side 64 which is convex in shape, and one side 65 which is concave.

A preferred maximum length for the electrode shown in FIG. 3 is of the order 50 mm, and preferred widths are in the range 20 to 40 mm, preferably in three sizes of widths 20 mm, width 30 mm and width 40 min.

Referring to FIG. 4, a second embodiment electrode has a plug 51 or a pigtail 52, 53 similarly as above, and is of similar maximum dimensions as the first electrode.

A third embodiment electrode as shown in FIG. 5 is of a "kidney" type shape, has either a plug 51 or pigtail 52, 53 and is preferably of external maximum dimensions of the same order as the electrode of FIG. 3.

Although the above dimensions are preferred, it is anticipated that some variation in dimensions of up to plus or minus 100% may suit the wide variety of naturally occurring sizes and shapes of the perineal body.

Referring to FIG. 6 of the accompanying drawings, an electrode suitable for fitting to the sacral region is shown. The electrode is of knitted or woven conductive cloth, similar to the above mentioned electrode, and is of a generally truncated triangular shape in plan view. The electrode has a base width of around 67 mm, a height of around 70 mm and a apex plateau region 200 of width around 15 mm. The plateau region has a dipped portion for placement of a finger to aid in positioning of the electrode over the sacrat spinous processes of S2, S3 and S4. The electrode is provided with a pigtail electrical contact lead 201 of length around 54 mm, terminating in a plug connector 202.

Figure 7:
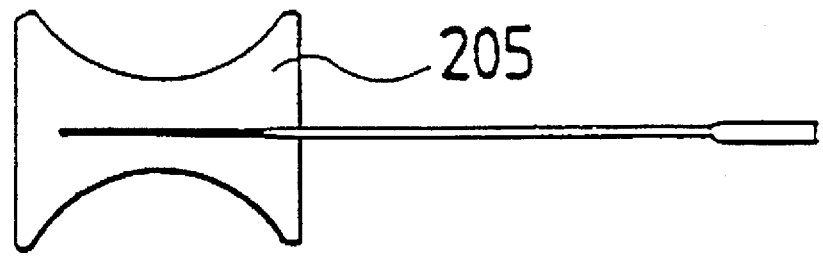
FIG. 7 shows an electrode for positioning in the perineal region, according to another embodiment of the present invention.

Referring to FIG. 7 of the accompanying drawings a surface electrode suitable for fitting to the perineal region comprises a sheet of conductive woven or knitted material in the shape of an hour glass 205, having a length of around 50 mm and a width of around 40 mm. The neck of the hour glass shaped electrode is preferably of width around 16 mm, and a pigtail lead of length around 92 mm is provided. Preferably, the pigtail lead is attached at the side of the electrode as shown in FIG. 7, for hygiene and ease of fitting.

Referring to FIG. 8, a structure of an electrode pad is shown. The pad comprises a woven or knitted conductive cloth 80, coated in a conductive adhesive gel 81. The adhesive gel may be of a known type, The cloth 80 is coated by a water proof backing 82, which is for example a plastics sheet material. The water proof backing is attached to the cloth by an adhesive layer 83. A conducting wire 84 in the form of a pigtail lead is electrically and physically attached to the cloth 80. A drive signal is transmitted along the pigtail to drive the electrode. The electrode pad has a press-stud 85, which may be used for aiding placement of the pad using a strap or the like. The stud may be electrically conducting and contact the cloth 80 such that a drive signal may be supplied via the stud in addition to or in alternative to the pigtail lead 84.

Figure 9:
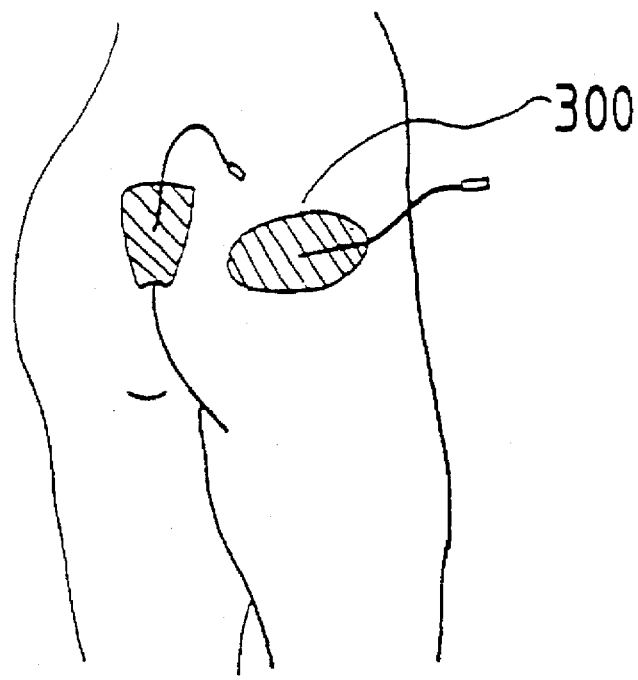
FIG. 9 shows one way of positioning the sacral electrode of FIG. 6 on a patients skin.

Referring to FIG. 9 of the accompanying drawings, placement of the sacral surface electrode of FIG. 8 is shown schematically, in combination with a further surface electrode 300 placed on a buttock of the patient, the further electrode being an indifferent electrode.

Preferably the sacral surface electrode is positioned over the sacrat spine S2–S4. Placement of the indifferent electrode is optional.

Figure 10:
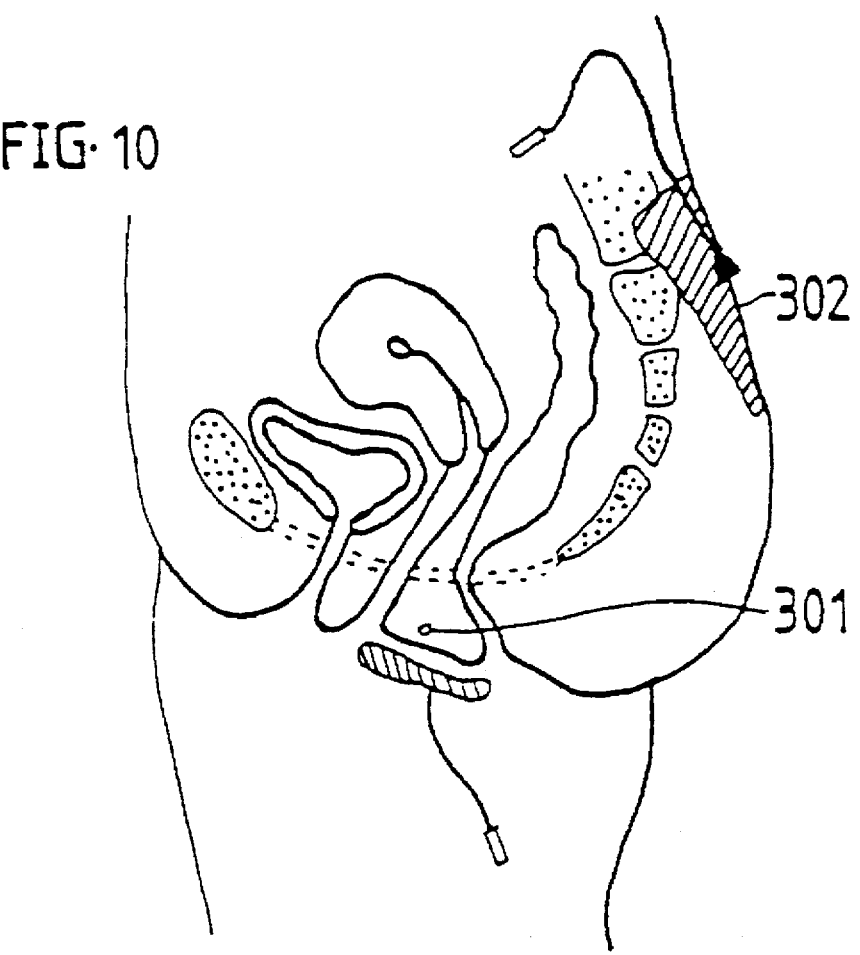
FIG. 10 shows one way of positioning the perineal electrode of FIG. 7 on a patients skin.

Referring to FIG. 10 of the accompanying drawings, the perineal surface electrode as described with reference to FIG. 8, is shown positioned over the perineal body of a patient to provide stimulation to the dorsal and perineal branches of the pudendal nerve 301. The sacral electrode 302 is also shown in position.

Any of the above electrodes may be reusable or disposable.

Use of the apparatus described with reference to FIGS. 1 to 10 will now be described, referring also to FIGS. 11 to 26.

In use, for treating urinary incontinence, one or more of the above electrodes are deployed over a perineal body between (in a female) the vagina and the anus. It is important that the electrode remains firmly in position during normal movement and is flexible enough to accommodate such movement. The use of a knitted or woven conductive material with a conductive adhesive gel in an electrode of shape specifically adapted for the perineal region may provide the necessary comfort and secure fixing to allow treatment of incontinence by a cutaneous electrode to be acceptable to the patient.

The electrical stimulation drive signal may be constructed as a combination of one or more signal per pulse geometries. Examples of such signal pulse geometries which may be selected according to instructions on the smart card are shown in FIGS. 11 to 19. For example FIG. 11 shows a simple Galvanic type wave form. FIG. 12 shows a simple sinusoidal waveform. FIG. 13 shows a square monophasic waveform. FIG. 14 shows a square waveform. FIG. 15 shows a square bi-phasic waveform. FIG. 16 shows a pulsatile (asymmetric balanced) wave form. FIG. 17 shows a Faradic waveform. FIG. 18 shows a monophasic sawtooth spike wave form, and FIG. 19 shows a bi-phasic sawtooth spike, wave form.

The Pulse Width may be selectable from, for example, any one of 80, 160, 200, or 320 μsec widths. The Pulse Envelope frequency may be selected from any one of three types. Type one is a regular fixed frequency rate, for example 10 Hz. Type two is a sequential rate rising or falling from a preset starting frequency to a preset final frequency. Type three is a randomly generated frequency rate with pulse separations occurring randomly between preset start and end frequencies. The pulse envelope duration may be selected from a range including for example 100, 250, 500, 750, or 1,000 μsecs. The Exercise/Relax cycle is similarly variable and the initial and final intensity voltages may be adjustable to provide a smooth ramp up and down for patient comfort. The overall treatment time is variable and the intensity may be selectable from the following ranges: 0–30 mA, 0–60 mA, or 0–100 mA.

Referring to FIG. 20 of the accompanying drawing, an example of a portion of a specific output drive signal waveform in accordance with specific pre-programmed instructions is shown. The example shown comprises a square monophasic waveform having a pulse burst duration of 100 μsecs and a frequency of 2 Khz. The pulse width is 80 μsecs and the period between bursts is 99 ms. The intensity (the height of the pulse in FIG. 11) is adjustable by the patient in the range 0–60 mA. Other portions of the drive signal waveform may have a frequency in the range 1 Hz to 2 KHz.

Figure 21:
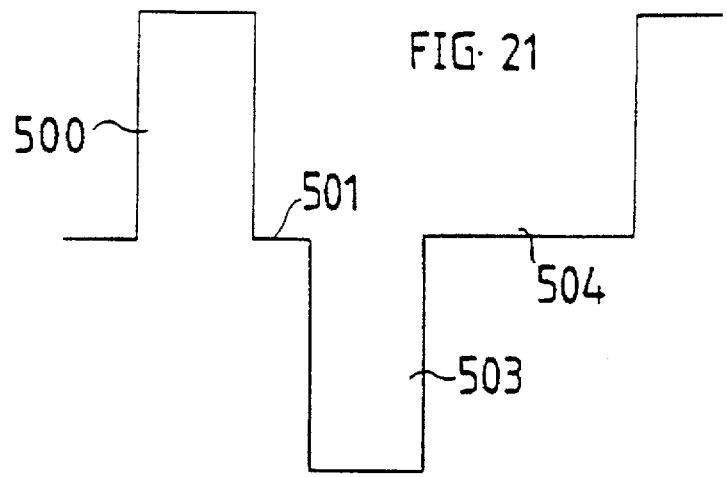
FIG. 21 shows as an example according to the present invention, a part of an electrical stimulation drive signal in the form of a preprogrammed pulse train.

Referring to FIG. 21 of the accompanying drawings, a typical preprogrammed bi-phasic pulse train is shown. The pulse train comprises a first pulse 500 of duration time T1, an inactive period 501 of duration time T2, a second pulse 503, of an opposite sense to the first pulse 500, and of duration time T3, and a second inactive time T4, the second inactive time being variable according to the frequency selected. The times T1, T2 or T3 are variable but typically may be T1=200 μsecs, T2=100 μsecs, T3=200 μsecs.

Figure 22:
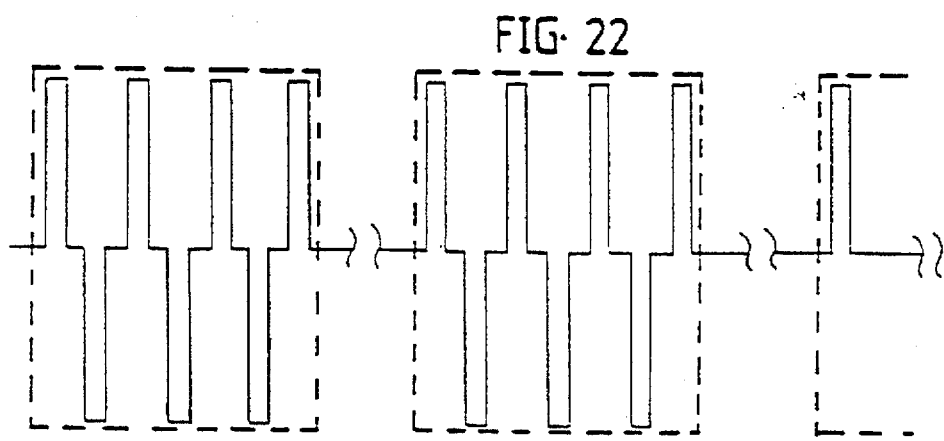
FIG. 22 shows as an example according to the present invention, a part of an electrical stimulation drive signal having a bi-phasic pulse train envelope.

Referring to FIG. 22, a preferred form of bi-phasic pulse is shown in an envelope train. The envelope duration is preferably in the range 100 to 1,000 μsecs, and N pulses per envelope are provided, N preferably being in the range 1 to 1,000. The envelope frequency FR2 can be sequential, random or fixed and is typically in the range 0.1 to 100 Hz. The period between repetitions of pulse packets. FR1 typically corresponds to a frequency of 500 to 5,000 Hz.

Figure 23:
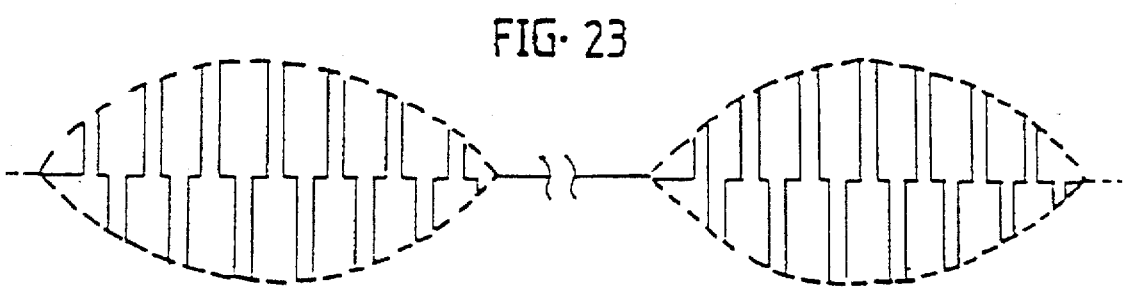
FIG. 23 shows as an example according to the present invention, a form of an electrical stimulation drive signal having a bi-phasic pulse train and a pulse train envelope which is modulated.

Referring to FIG. 23, a pulse train having a modulated envelope is shown. The modulation of the pulse train envelope can be any suitable shape. The duty cycle of the envelope, within the envelope period defined by the envelope frequency FR2, is preferably in the range 1 to 99%.

Figure 24:
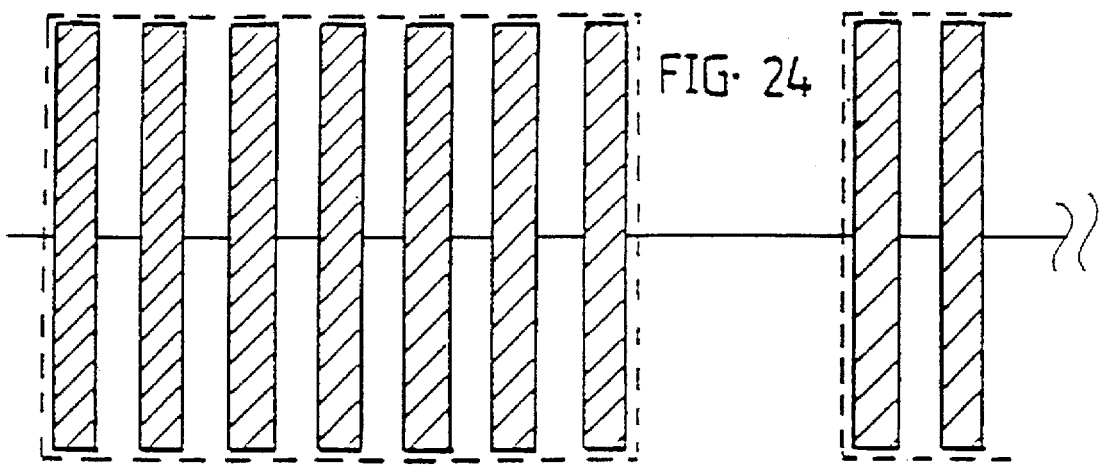
FIGS. 24 to 26 show the preselected pulse geometry delivered in various pulse envelopes timed over predetermined execise and relax periods, the voltage intensity in the initial and final time periods within each exercise and relax phase may also be ramped up or down for additional patient comfort.

Referring to FIG. 24 of the accompany drawings, an example of a uniform (fixed) rate envelope is shown. A preselected pulse geometry of pulses being spaced apart by 2 μsecs, with a preselected pulse geometry of either a monophasic or bi-phasic, and either a square or random characteristic is selected.

Figure 25:
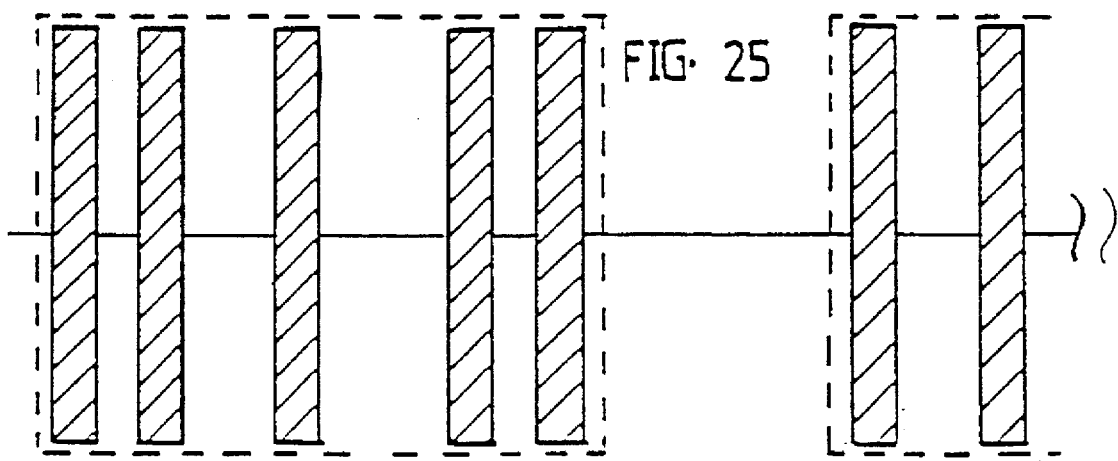

FIG. 25 shows a random generated envelope sequence in which pulses within the envelope are randomly spaced apart from each other, in this example by a period between a first and second pulse being 2 μsecs, the period between the second and third pulse being randomly selected as 10 μsecs, the period between the third and fourth pulse being randomly selected as 6 μsecs, between the fourth and fifth pulse the time is randomly selected as 2 μsecs, and between the fifth and sixth pulse the time is randomly selected as 4 μsecs. In a succeeding pulse envelope, the times between the pulses within the envelope are randomly selected again, and are different from those in the first envelope shown.

Use of a randomly generated pulse train within a fixed pulse envelope may have an advantage that the human body does not become acclimatised to the particular form of treatment. The patients body may maintain its response to the treatment, which has no predictable pulse pattern within the pulse envelope, over an indefinite period, without significant loss of effectiveness.

Figure 26:
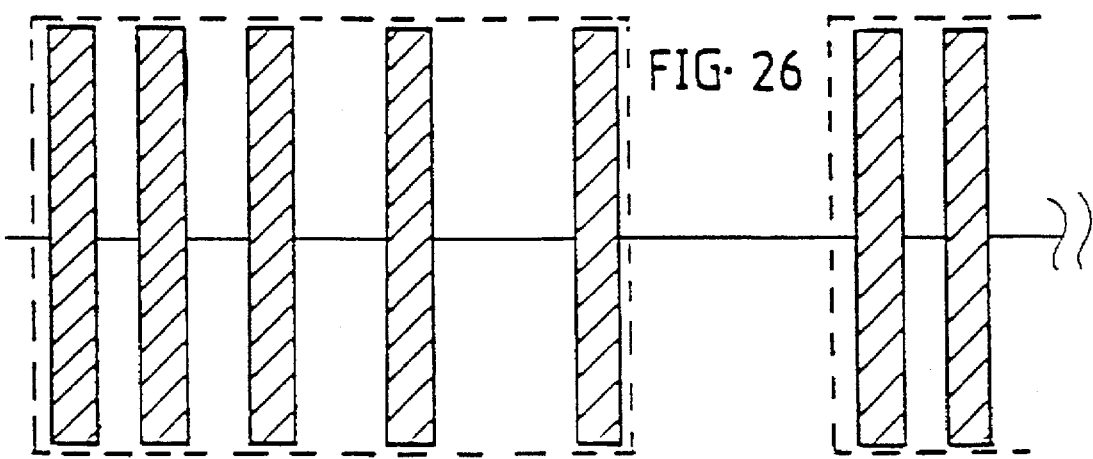

Referring to FIG. 26 of the accompanying drawings, a set of sequentially generated envelopes are shown in which the exercise phase (i.e. the period occupied by the pulse envelope), and the relax phase are variable. This is equivalent to varying the position in time of the pulse envelope within the duty cycle. In the example shown, within the pulse envelope, the pulses are ordered such that the second pulse is spaced from the first pulse by a time of 2 μsecs, the time elapsed between the second and third pulses is 4 μsecs, the time elapsed between the third and fourth pulses is 6 μsecs, and the time elapsed between the fourth and fifth pulses is 8 μsecs. This pattern is repeated in successive sequentially generated envelopes.

Hereinabove, FIGS. 24 to 26 have shown the exercise/relax cycles with a constant amplitude at start and finish. This may be replaced with a gradual ramp up/down over a preselected period similar to that shown in FIG. 24.

Various other electrodes, of the insertable type, will now be described.

Figure 27:
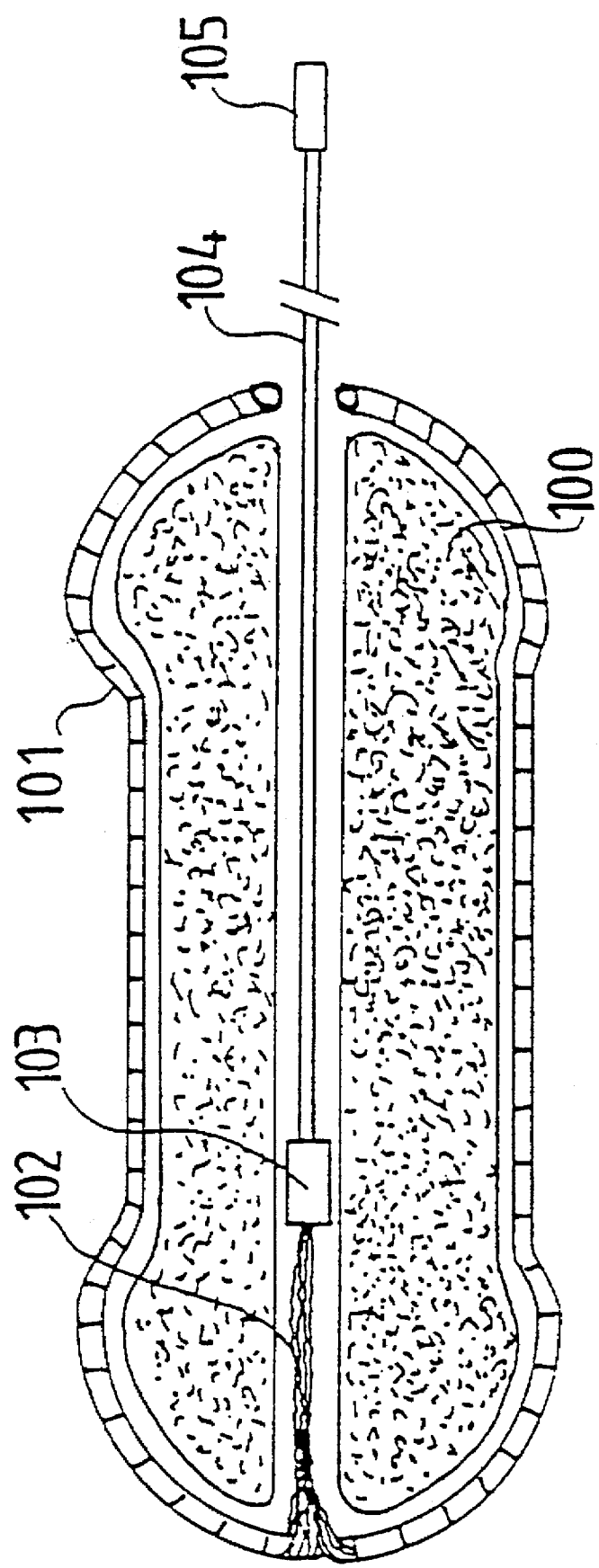
FIG. 27 shows a first insertable electrode for internal use, according to an embodiment of the present invention.

Referring to FIG. 27 of the accompanying drawings, a first insertable electrode comprises an inner core moulded from a resilient and deformable material such as a foam, or paper/cotton fibre 100 and an outer conductive sheath 101 of knitted or woven conductive fibre, for example stainless steel fibre, or metallized plastic fibre. The outer conductive sheath surrounds the inner core 100. Individual fibres of the outer conductive sheath are gathered into a thread 102 and connected via a crimp connection 103 to a flexible pigtail connector wire 104 of, for example, silicon rubber coated wire. The flexible pigtail connector wire has at one end a plug 105 for connection to a drive u The material of the inner core 100 and the outer conductive sheath 101 are deformable to allow compression and insertion of the electrode into a hollow tubular applicator (not shown). A suitable core material has a Shore hardness of below 45, and is deformable enough so as to be compressed to 75% or less of its unrestricted size. In an electrode of dimensions suitable for insertion into a vaginal or rectal tract, a surface of the foam is preferably depressible by at least 1.5 mm.

Biocompatible fibres may be used in the construction. For example Biocompatible Polyvinyl Formal (PVF) foam, cotton or paper materials.

The electrode may be manufactured as a single moulded flexible conductive foam or as a moulded PVF foam plug surround by flexible conductive woven or knitted cloth sheath. In this latter embodiment, the sheath may be incorporated during the moulding phase of manufacture or may be fitted after moulding.

The electrode may alternatively be manufactured as a moulded PVF foam as above, but with an inner plug manufactured from fibrous paper or cotton material.

In use, the applicator, containing the electrode, is inserted into either a vaginal or anal tract, to position the electrode therein. The applicator is then withdrawn, without moving the electrode. Once released, the foam material of the electrode expands to provide close contact with an internal wall of the vaginal or anal tract. A lubricating gel may be used during insertion and/or extrusion of the applicator to aid deployment. The gel may be conductive.

The electrode may be washable or disposable.

Referring to FIG. 28, a second insertable electrode comprises an elongate substantially cylindrical core of a resilient deformable material 100 as aforementioned with reference to FIG. 27, having a tubular band of conductive material 101 which surrounds and constricts a mid portion 109 of the core. At either end of the band, portions of the core 110, 111, which are unrestrained by the band 101 relax to adopt an uncompressed diameter greater than the diameter of the constricted mid portion of the core 109.

The mid portion 109 of the core may be further compressible by compressing the conductive material 101, but is restricted from substantial expansion to a fully relaxed state by the band 101.

The tubular band is of length in the range 15 to 20 mm, the overall length of the core being suitably in the range 50 to 60 mm and the relaxed diameter of the core being in the range 20 to 30 mm. These dimensions may be varied to accommodate natural anatomical variations.

The second electrode has an hollow tubular passage 108 centrally, for accommodating a rigid rod centrally in the core. Using this rod, the electrode may be pushed into the tract without the need for an enclosing applicator as described with reference to FIG. 28. In this mode of deployment, the end portions 110, 111 of the core, and/or the mid portion 109 may be squeezed during insertion, and then expand when in place in the tract.

However, the embodiment is not restricted to this mode of deployment and may be inserted in a hollow applicator as aforementioned with reference to FIG. 28, and may retained in the tract during removal of the applicator by the insertion of the rod in the hollow passage 108. The rod is subsequently removed.

The second insertable electrode has a contact lead 104 and plug 105 for making electrical connection to the conductive material 101 and for use in removing the electrode from the tract.

Referring to FIG. 29, a third insertable electrode is of similar construction to the second electrode, but, a tubular band 130 of conductive material of length in the range 6 to 12 mm is provided.

Referring to FIG. 30, a fourth insertable electrode is of similar construction to the above mentioned first insertable electrode, of FIG. 28, however, in the fourth insertable electrode, a hollow passage 108 is provided in the core 131 for insertion of a rigid rod, similarly as described with reference to the second insertable electrode.

Referring to FIG. 31, a fifth insertable electrode comprises a core of flexible material 100, similarly as described with reference to FIG. 29, and first and second tubular bands 150, 151 each of a conductive material as described hereinabove with reference to FIGS. 18 to 21. Each conductive band 150, 151 is connected to a respective first and second conductor leads 152, 153, in a manner as hereinabove described.

Preferably, the conductive bands are each of length 6 mm or thereabouts, and separated by a distance of 8 mm, although these dimensions and lay outs are not restrictive and may be varied. During treatment, the inflatable tampon electrode may be used periodically to monitor progress and provide encouragement for the patient to continue.

The fifth electrode may be deployed as previously described hereinabove with reference to FIG. 28.

In use, the fifth electrode may be electrically driven via the first and second leads 152, 153 by respective first and second drive signals. The first and second drive signals need not be identical, and preferably have different parameters. Such an electrode may be suitably useable in FES treatment.

Referring to FIG. 32, a structural portion of an insertable electrode is shown. Such a structure may be incorporated into any one or more of the insertable electrodes as described with reference to FIGS. 27 to 31 as hereinabove described.

The structure comprises a core of foam material 100, such as hereinabove described, an electrically insulating backing material 140, for example a sheet material, an adhesive layer 141, and a conductive fibre material 142. The insulating backing material and adhesive layer are sandwiched between the conductive material and the core.

A connecting lead 143, in the form of a pigtail wire, is incorporated into the structure, making electrical contact with the conductive material 142. The connection is of sufficient strength to enable the insulating electrode to be pulled using the connecting lead, without the connecting lead coming loose from the structure. Additionally, the lead may be woven into or otherwise attached to the conductive fibre 142, similarly as herein described with reference to cutaneous electrodes.

Figure 33:
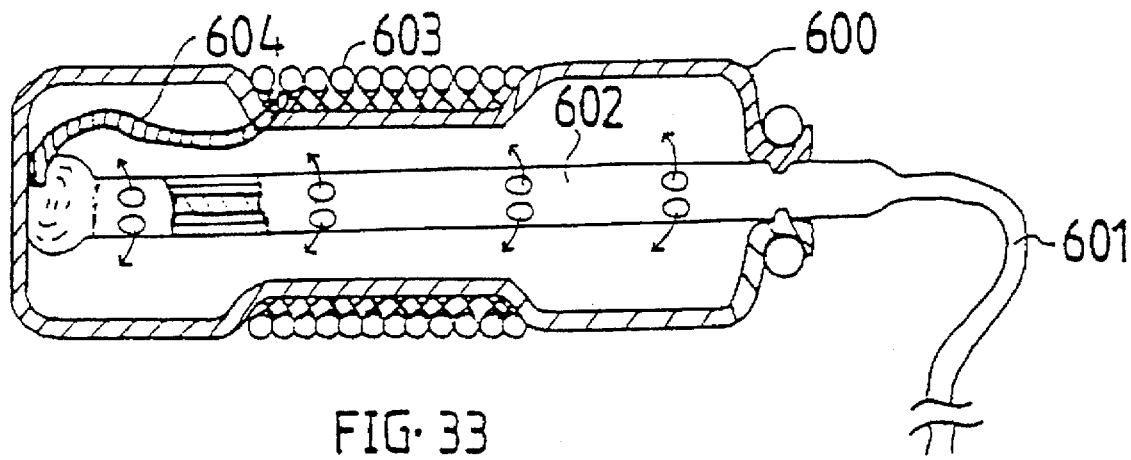
FIG. 33 shows an inflatable electrode according to a specific embodiment of the present invention.

Referring to FIG. 33 of the accompanying drawings, an inflatable tampon electrode for insertion into the vagina or anus of a patient is shown, the electrode having an outer sheath 600, of a rubber silicon material, the outer sheath being inflatable or deflatable by air which is pumped in through a delivery pipe 601 and a rigid internal member 602, and a woven or knitted conductive cloth 603 bonded to the outer surface of the rubber sheath 600. The conductive sheath is connected to external sensing apparatus by an electrically conductive lead wire 604 which runs through the centre of the rigid member and the hollow air delivery pipe 601.

Figure 34:
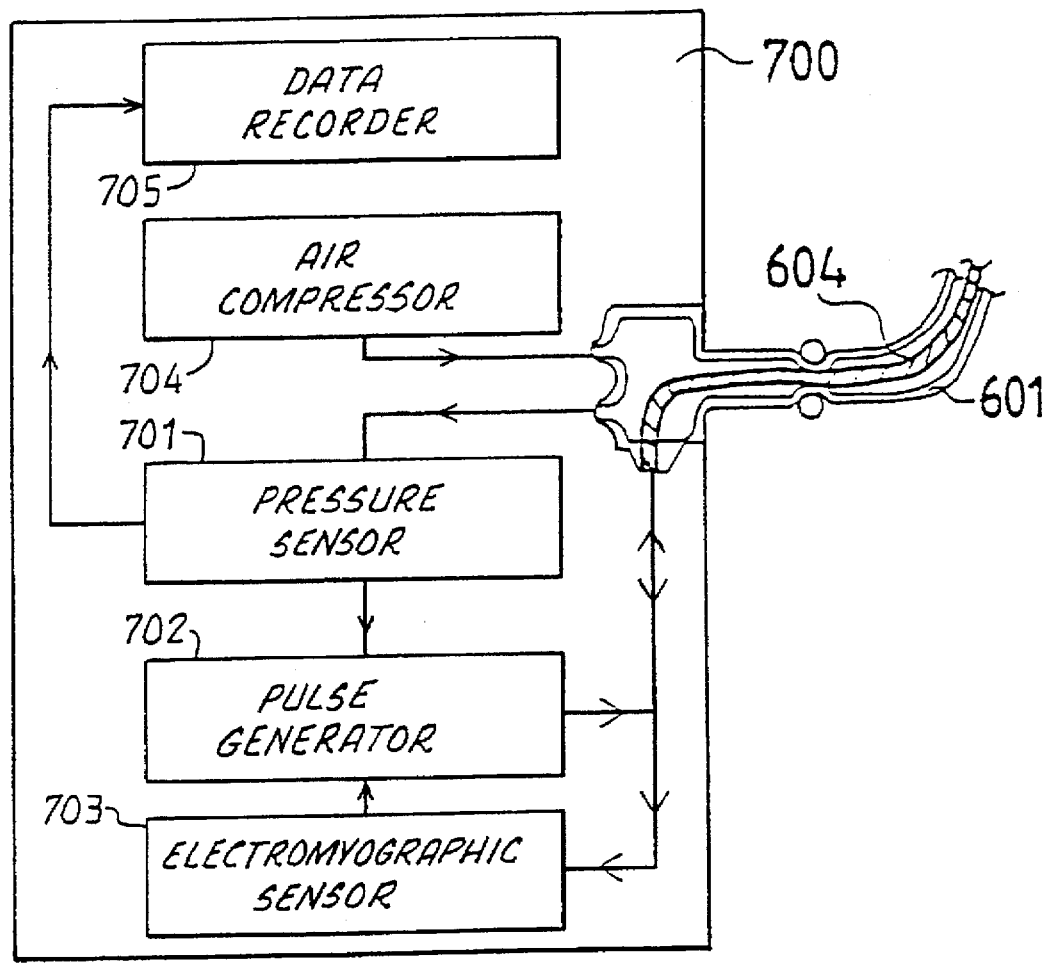
FIG. 34 shows a sensing apparatus according to a specific embodiment of the present invention.

Referring to FIG. 34 of the accompanying drawings, the other end of the delivery pipe 601 and connecting lead 604 enter a sensing apparatus 700. The sensing apparatus comprises a pressure sensor 701, a pulse generator 702, an electromyographic sensor 703, an air compressor 704, and a display and data recorder 705.

The tampon electrode of FIG. 33 and the sensing apparatus of FIG. 34 are used in various modes as follows. Firstly, the air compressor is run continuously to inflate the inflatable tampon electrode of FIG. 33. A patient is encourage to squeeze the tampon electrode, and changes in air pressure are detected by the pressure sensor 701 and displayed by the display and data recorder 705. Thus a measure of the strength of a patient's muscles can be determined by the read out on the display and data recorder 705. Alternatively, the patient can be asked to squeeze the electrode, and the number of strokes of the air compressor counted in order to reach a predetermined pressure. This number of strokes will also give a measure of the condition of the patient's muscles.

In a facilitation mode, the patient is encouraged to squeeze the electrode, which is inflated by the air compressor 70, when squeezing of the electrode is detected by either a pressure difference monitored by the pressure sensor 701, or by a difference in the amount of work the air compressor needs to do to keep the electrode inflated, then the pulse generator generates a signal in response to either of these two detected parameters and transmits this along the conductive lead 604 to electrically stimulate the muscles. This results in further contraction, aiding the patient in their squeezing action. Additionally, the pulse generator may be activated in response to an output from the electromyographic or perineometer sensor 703.

Any one or more of the above described internal electrodes can be used to perform Pelvic Floor Exercises. The preferred method is by using the embodiment of FIG. 33 in conjunction with Bio feedback and Facilitated Electrical Stimulation. In such exercise, a (female) patient, practices squeezing exercises by squeezing and relaxing against the resilience of the electrode.

The patient exercises by working muscles against the resilience of the core material, rather than by attempting to keep the core in situ.

Variations in the resilience and deformability of the core material 100 maybe made to suit various exercises. A series of electrodes may be provided, each electrode being of a progressively increased deformability and/or resilience to provide a means of performing a programme of progressively more advanced exercises.

In the above described embodiments of insertable electrodes, the outer conductive sheath may be completely conductive over the whole of its surface, or may comprise one, two or more conductive bands incorporated therein. In either case, the conductive material contacts the wall of the tract to deliver an electrical signal thereto. The sheath may be constructed from flexible woven or knitted cloth or may be of stitched construction using conductive fibres. The sheath may be sewn or bonded to the core.

In each embodiment of the internal electrode, the connecting pigtail wires are preferably sewn or crimped to the sheath to be used for pulling the electrode during removal from the cavity.

A main advantageous feature of the various of the above embodiments may be an ability to multiplex facets an individual patient's treatment programme. For example, in Stress incontinence, the patient may follow a particular set of preset instructions for NTS treatment which would be intended to restore a pudendal nerve function and regenerate type I slow muscle fibres.

The treatment can be applied via a cutaneous perineal electrode and an arbitory indifferent electrode positioned on the buttock, thigh or abdomen, with the treatment pulse preset to a specified set of parameters by the smart card selected for this aspect of treatment.

In later weeks the treatment may require that the type I slow fibres require additional strengthening and the electrode system could then be changed for NMS treatment, by passing the pulse between the single banded tampon electrode and either a cutaneous perineal or arbitory indifferent electrode. The electrical parameters for the electrode drive signals could be provided in accordance with appropriate instructions contained in a second smart card.

At the end of the treatment, it may then be preferable to add to the strength of the type It fast fibres which may best be achieved by FES treatment, applied using a single double banded tampon electrode driven by a new selected drive signal in accordance with new instructions contained in a third smart card.

The final part of the treatment may include use of the bio-feedback facility.

Thus, a flexible treatment apparatus and system may be provided, using a single piece of equipment. In contrast, using prior-art systems, a patient would possibly only receive one of the aforementioned modes of treatment, or alternatively, three separate sets of equipment would be necessary.

Specific embodiments of the invention may have an advantage of providing variable combinations of pulse geometry, intensity ceilings and preset treatment parameters to suit, in addition to urinary or faecal incontinence treatment, therapeutic requirements including Transcutaneous Electrical Nerve Stimulation (TENS), Functional Electrical Stimulation (FES), Neuro Muscular Stimulation (NMS), Neuro Trophic Stimulation (NTS), Interferential Therapy, Iontophoresis or Galvanism.

Specific embodiments of the invention may provide a versatile apparatus which provides a combination of electro-stimulation treatments available in a single unit. The module may have an advantage of being easily set by a clinician to provide a prescribed electro-stimulation treatment, yet be tamper proof by a patient.

Various of the embodiments may have an advantage of being capable of recording details of the administration of a prescribed treatment such that clinician can periodically monitor such administration when the patient is out of clinic.

The embodiments may advantageously provide an electro-stimulation apparatus which is portable by a patient, and can be preset to provide a drive signal having fixed parameters selected from a range of selectable drive signal parameters.

Specific embodiments of the present invention may have an advantage of providing means of treatment for incontinence using a flexible sheet material electrode.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specication (including any accompanying claims, abstract and drawings, or to any novel one, or any novel combination, of the steps of any method or process so disclosed.

We claim:

1. A sacral surface electrode for application of electrical stimulation to patients suffering from incontinence, said sacral electrode comprising:

a conductive material;

means, defining a shape of said conductive material, for fitting said sacral electrode to a surface sacral region of said patients for stimulating nerves in the sacral region wherein said conductive material has a shape of a generally truncated triangle and wherein the conductive material includes an apex plateau region and means, defining a dipped portion, for facilitating finger placement of the sacral surface electrode over the sacral region; and means for connecting said conductive material to a source of electrical stimulation pulses.

2. Apparatus for application of electrical stimulation to patients suffering from incontinence, said apparatus comprising:

generator means for providing a series of electrical stimulation pulses;

tampon electrode means, responsive to said series of electrical stimulation pulses, for causing muscle contraction in order to reduce patient incontinence, said tampon electrode means comprising an electrically conductive outer sheath and means for expanding and contracting the outer sheath to enhance conduction of the electrical stimulation pulses into a vaginal or anal wall of the patient by conforming the outer sheath to the vaginal or anal wall; and sacral surface electrode means, shaped for fitting to a sacral region of said patient and responsive to said series of electrical stimulation pulses, for stimulating nerves in the sacral region.

3. The apparatus according to claim 2 wherein the means for expanding and contracting the outer sheath comprises means for pneumatically expanding and contracting the outer sheath.

* * * * *